United States Patent [19]

Herter et al.

[11] Patent Number: 4,666,921

[45] Date of Patent: May 19, 1987

[54] PYRAZOLE DERIVATIVES, PROCESSES FOR THEIR PREPARATION AND PHARMACEUTICAL PREPARATIONS CONTAINING THESE COMPOUNDS

[75] Inventors: Rolf Herter, Schwabach; Helmut Schickaneder, Eckental; Peter Mörsdorf, Cadolzburg; Stefan Postius, Nürnberg; Istvan Szelenyi, Schwaig; Kurt H. Ahrens, Nürnberg, all of Fed. Rep. of Germany

[73] Assignee: Ludwig Heumann & Co. GmbH, Nuremberg, Fed. Rep. of Germany

[21] Appl. No.: 787,114

[22] Filed: Oct. 15, 1985

[30] Foreign Application Priority Data

Oct. 17, 1984 [DE] Fed. Rep. of Germany ....... 3438072

[51] Int. Cl.$^4$ ................. A61K 31/445; A61K 31/415; C07D 401/12; C07D 403/12

[52] U.S. Cl. .................................. 514/326; 514/210; 514/407; 546/211; 548/374; 548/376; 548/950

[58] Field of Search ................ 546/211; 548/374, 376; 514/326, 407

[56] References Cited

U.S. PATENT DOCUMENTS 4,337,263 6/1982 Techer et al. ...................... 348/376

Primary Examiner—Robert T. Bond
Attorney, Agent, or Firm—Burns, Doane, Swecker & Mathis

[57] ABSTRACT

Special pyrazole derivatives corresponding to the general formula I which have a highly selective action on histamine-$H_2$ receptors are described. Compared with other drugs known to be effective in their action on histamine-$H_2$ receptors, these compounds have improved pharmacological properties. A method of preparation of these compounds is also described.

5 Claims, No Drawings

PYRAZOLE DERIVATIVES, PROCESSES FOR THEIR PREPARATION AND PHARMACEUTICAL PREPARATIONS CONTAINING THESE COMPOUNDS

DESCRIPTION

This invention relates to new pyrazole derivatives which have a highly selective action on histamine $H_2$ receptors, to processes for their preparation and to pharmaceutical preparations containing these compounds and to the use of these compounds in therapy.

Cimetidine and ranitidine have already been used therapeutically as anti-ulcerative agents. Both these substances, however, have a relatively short half life and are therefore required to be administered in several daily doses of tablets with dose units of 160–300 mg each in a therapeutically fixed form. There continues to be a need for anti-ulcerative agents which are superior in their overall pharmacological properties to cimetidine and ranitidine. By virtue of their specific $H_2$-antagonistic activity, the compounds according to the invention inhibit gastric secretion which has been stimulated by histamine agonists. Ash and Shild, "Brit. J. Pharmocol. Chemotherapy", 27, 427 (1966) and Black et al "Nature", 236, 385 (1972).

The pharmacological activity of these compounds may be demonstrated on the perfused rat stomach by a modified method according to DE OS No. 2,734,070 or by determining the $pA_2$ values in vitro on the atrium of the guinea pig (see Ariens, Molecular Pharmacology, Volume 1, Academic Press, New York, 1964). The $H_2$-antagonistic action can also be demonstrated on waking Heidenhain-Pouch dogs by the method of Black et al, "Nature" 236, 385 (1972) and waking fistulated cats.

The new compounds also antagonise the action of histamine on the frequency of contraction of the isolated right atrium of the guinea pig but have no influence on histamine induced contractions of isolated, smooth gastrointestinal muscle if these contractions have been produced by $H_2$— agonists. Since substances which inhibit histamine-$H_2$ receptors have an inhibitory action both on the basal gastric secretion and on the gastric secretion induced by gastrin, histamine, metacholine or food, they may be used for the treatment of peptic ulcers caused by excessive gastric acid secretion as well as for the treatment of hyperacidic gastritis.

The present invention is based on the object of providing new inhibitory substances for histamine-$H_2$ receptors with improved activity. This problem is solved by the present invention.

The present invention thus relates to new pyrazole derivatives corresponding to the general formula I

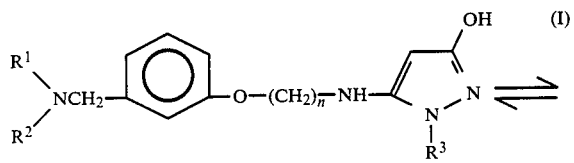

-continued

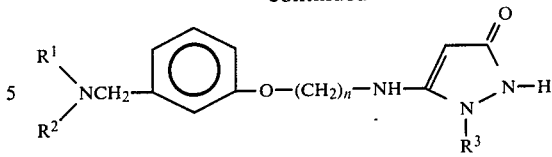

wherein $R^1$ and $R^2$ denote, independently of one another, a hydrogen atom or a straight chained or branched $C_1$-$C_3$ alkyl group or $R^1$ and $R^2$ together with the nitrogen atom form a 4- to 7-membered alicyclic heterocyclic group containing nitrogen, n represents an integer having a value from 2 to 6, and $R^3$ denotes a hydrogen atom or a methyl or ethyl group, and to the physiologically acceptable salts and hydrates thereof.

In the general formula I, $R^1$ and $R^2$ denote, independently of one another, a hydrogen atom or a straight chained or branched $C_1$-$C_3$ alkyl group. Examples of such straight chained or branched alkyl groups include the methyl, ethyl, i-propyl and n-propyl group, the methyl group and ethyl group being preferred. The substituents $R^1$ and $R^2$ may, however, also combine with the nitrogen atom to which they are attached to form a nitrogen-containing heterocyclic ring having 4-7 members. Examples of such rings include the acetidine pyrrolidine, piperidine and homopiperidine ring, the pyrrolidine ring and piperidine ring being preferred. The symbol n represents an integer having a value from 2 to 6, preferably 3. $R^3$ represents a hydrogen atom or a methyl or ethyl group, preferably a methyl group.

A preferred group of compounds according to the invention is characterised in that the general formula I, $R^1$ represents a hydrogen atom and $R^2$ also represents a hydrogen atom or it represents a straight chained or branched $C_1$-$C_3$ alkyl group, e.g. a methyl, ethyl, propyl or isopropyl group.

Another preferred group of compounds according to the invention is characterised in that $R^1$ represents a straight chained or branched $C_1$-$C_3$ alkyl group such as, for example a methyl, ethyl or propyl group, in particular a methyl group, and $R^2$ also represents a straight chained or branched $C_1$-$C_3$ alkyl group, preferably a methyl group.

Yet another preferred group of compounds according to the invention is characterised in that both $R^1$ and $R^2$ represent methyl.

The following are examples of preferred compounds:
1-methy-5-[3-[3-(piperidinomethyl)phenoxy]-propylamino]-3-hydroxy-1H-pyrazole,
1-methyl-5-[3-[3-(pyrrolidonomethyl)phenoxy]-propylamino]-3-hydroxy-1H-pyrazole,
1-methyl-5-[3-[3-(dimethylaminomethyl)phenoxy]-propylamino]-3-hydroxy-1H-pyrazole,
1-methyl-5-[4-[3-(piperidinomethyl)phenoxy]-butylamino]-3-hydroxy-1H-pyrazole,
1-methyl-5-[4-[3-(pyrrolidinomethyl)phenoxy]-butylamino]-3-hydroxy-1H-pyrazole,
1-methyl-5-[6-[3-(piperidinomethyl)phenoxy]hexylamino]-3-hydroxy-1H-pyrazole, and
5-[3-[3-(piperidinomethyl)phenoxy]propylamino]-3-hydroxy-1H-pyrazole.

The compounds according to the invention may exist in various tautomeric forms corresponding to the above pair of formulae. The invention is therefore intended to cover all tautomeric compounds as well as the physiologically acceptable hydrates and salts thereof. The salts are prepared with inorganic or organic acids in known manner. These salts may be, for example, salts of mineral acids such as hydrochloric, hydrobromic and hydroiodic acid, phosphoric acid, metaphosphoric acid, nitric acid or sulphuric acid or salts of organic acids such as formic acid, acetic acid, propionic acid, phenyl acetic acid, tartaric acid, citric acid, fumaric acid, methane sulphonic acid, etc.

The compounds according to the invention may be prepared by a process which is characterised in that a compound corresponding to the general formula II

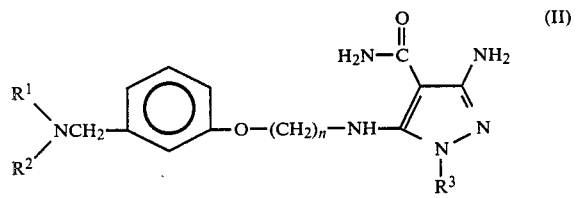

wherein $R^1$, $R^2$, $R^3$ and n have the meanings indicated above is reacted in aqueous acid solution to form a compound according to the invention corresponding to the general formula I, the compound thus obtained being optionally converted into a physiologically acceptable salt thereof.

The reaction may be carried out, for example, in concentrated, aqueous hydrochloric acid solution at reflux temperature. The reaction time is several hours, for example, 18 hours. The desired compound is worked up and isolated by the usual methods, for example by chromatographic purification and crystallization.

Preparation of the intermediate products described hereinafter may be carried out by methods analogous to those of R. Gompper and W. Töpfl (Chem. Ber. 95, 2871 and Chem. Ber. 95, 2881 (1962)).

The compounds according to the invention may be incorporated in any suitable formulation for administration. The invention therefore also covers pharmaceutical preparations containing at least one compound according to the invention for use in human and veterinary medicine. Such pharmateutical preparations may be prepared by conventional methods using one or more pharmaceutically acceptable carriers or diluents.

The compounds according to the invention may therefore be formulated for oral, buccal, external, parenteral or rectal administration, oral administration being preferred.

For oral administration, the medicament may be provided, for example, in the form of tablets, capsules, powders, solutions, syrups or suspensions prepared with the aid of suitable diluents in known manner.

For buccal administration, the medicament may be provided in the form of tablets or sachets formulated in the usual manner.

For parenteral administration, the compounds according to the invention may be formulated to be given by bolus injection or by continuous infusion. Formulations for injection may be made up in unit doses as ampules or in multiple dose containers with added preservative.

The pharmaceutical preparations may assume forms such as suspensions, solutions or emulsions in oily or aqueous carriers and may contain formulation auxiliaries such as dispersing or suspending agents and/or stabilizers.

Alternatively, the active ingredient may be prepared in powder form to be reconstituted with a suitable carrier such as sterile, pyrogen-free water.

The compounds according to the invention may also be formulated for rectal administration, for example as suppositories or retention enemas which may, for example, contain the usual suppository excipients such as cocoa butter or other glycerides.

For external application, the compounds according to the invention may be formulated in the usual manner as ointments, creams, gels, lotions, powders or sprays.

For oral administration, a suitable daily dose of compounds according to the invention may be made up of one to four doses adding up to a total of from 5 mg to 1 g per day, preferably from 5 to 250 mg/day, depending on the condition of the patient. It may be necessary to deviate from these quantities in individual cases, depending on the individual response of the patient to the active ingredient or the nature of the formulation of the preparation and the time or intervals of time at which administration is carried out. In certain cases, for example, it may be sufficient to administer less than the minimum quantity indicated above whereas in other cases it may be necessary to exceed the upper limit indicated.

The compounds according to the invention are distinguished from known, reputable pharmaceutical preparations having a similar activity by their improved overall pharmacological properties. This is evident from the results of the pharmacological comparison tests given below.

Pharmacological Tests

Experimental model: waking fistulated cat (stimulator: histamine)
Cimetidine (comparison) i.V. $ID_{50}$ 1.4 μmol/kg
Example 1 i.V. $ID_{50}$ 0.03 μmol/kg

EXAMPLE 1

(a) Preparation of 2-cyano-3-methylthio-3-[3-[3-(piperidinomethyl)-phenoxy]propylamino]-propene nitrile

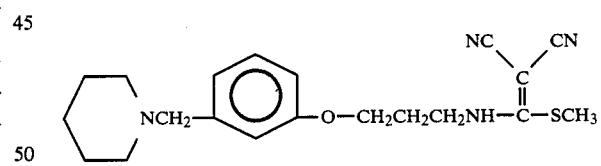

18.1 g (73 mmol) of 3-[3-(piperidinomethyl)phenoxy]-propanamine are added at room temperature to 12.4 g (73 mmol) of bismethylthio-methylene-malodinitrile in 200 ml of diethyl ether. Stirring is continued for a further 1 hour at room temperature and 1 hour under reflux and the solvent is then removed under vacuum. The pale red, viscous oil remaining behind is subjected to further reaction without purification.

Yield: 25.7 g (95% of theoretical)
RF: 0.45 ($Al_2O_3$ neutral; ethylacetate/petroleum ether
$C_{20}H_{26}N_4OS$ (370)
$^1$H-NMR-data: ($CDCl_3$, TMS as internal standard)
δ=1.50 L (m) 6 H, 2.15 (m) 2 H, 2.39 (m) 4 H, 2.56 (s) 3 H, 3.43 (s) 2 H, 3.83 (t) 2 H, 4.12 (t) 2 H, 6.5–7.4 (m) 5 H (1 H replaceable by $D_2O$) ppm.

(b) Preparation of 4-cyano-1-methyl-$N^5$-[3-[3-(piperidinomethyl)phenoxy]propyl[-pyrazole-3,5-diamine

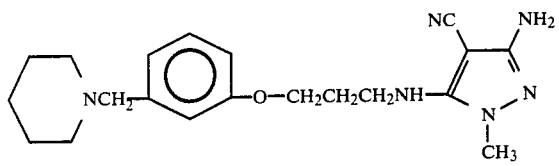

25.7 g (69 mmol) of 2-cyano-3-methylthio-3-[3-[3-(piperidinomethyl)phenoxy]propylamino]-propene nitrile are dissolved in 30 ml of ethanol and added at 85° C. to 40 ml of methyl hydrazine in 80 ml of water. Stirring is then continued at this temperature for 1 hour and the reaction mixture is left to cool slightly diluted with water and extracted with ethyl acetate. After dehydration over sodium sulphate, the organic phase is concentrated by evaporation and the oil remaining behind is crystallized from ethyl acetate/diethyl ether.

Colourless crystals, melting point 102°–104° C.

Yield: 16.8 g (66% of theoretical)

Rf: 0.46 (Al$_2$O$_3$ neutral; ethylacetate/isopropanol 95/5)

$C_{20}H_{28}N_6O$ (368)

$^1$H-NMR data: (d$_6$-DMSO, TMS as internal standard) $\delta = 1.42$ (m) 6 H, 2.00 (m) 2 H, 2.30 (m) 4 H, 3.30 (s) 3 H, 3.37 (s) 2 H, 3.2–3.65 (m) 2 H, 4.04 (t) 2 H, 4.98 (s) 2 H, (replaceable by D$_2$O), 6.42 (t) 1 H (replaceable by D$_2$O), 6.7–7.4 (m) 4 H ppm.

(c) Preparation of 4-Carboxamido-1-methyl-$N^5$[3-[3-(piperidinomethyl)phenoxy]propyl]-pyrazole-3,5-diamine

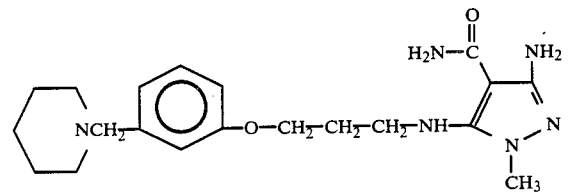

5.9 g (16.5 mmol) of 4-cyano-1-methyl-$N^5$-[3-[3-(piperidinomethyl)phenoxy]propyl]-pyrazole-3,5-diamine are boiled under reflux for 16 hours with 6.6 g of sodium hydroxide in 100 ml of 50% of ethanol. The reaction mixture is diluted with water and the product is extracted with ethyl acetate and dehydrated over sodium sulphate. The ochre coloured solid which remains behind after evaporation under vacuum is re-crystallized from ethyl acetate.

Colourless crystals, melting point 100°–102° C.

Yield: 3.8 g (60% of theoretical).

Rf: 0.35 (Silica gel; ethyl acetate/methanol/TEA 85/10/5)

$C_{20}H_{30}N_6O_2$ (386)

$^1$H-NMR data: (CDCl$_3$, TMS as internal standard) $\delta = 1.50$ (m) 6 H, 2.03 (m) 2 H, 2.37 (m) 4 H, 3.25–3.6 (m) 2 H, 3.43 (s) 2 H, 3.61 (s) 3 H, 3.95 (s) 2 H, (replaceable by D$_2$O), 4.08 (t) 2 H, 5.80 (t) 1 H (replaceable by D$_2$O), 6.19 (s) 2 H (replaceable by D$_2$O), 6.7–7.4 (m) 4 H ppm.

(d) 1-methyl-5-[3-[3-(piperidinomethyl)phenoxy]-propylamine]-3-hydroxy-1H-pyrazole and 5-amino-1-methyl-$N^5$-[3-[3-(piperidinomethyl)phenoxy]propyl]-1,2-dihydro-pyrazol-3-one

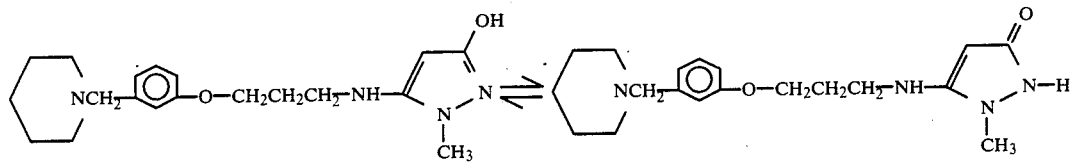

3.8 g (9.8 mmol) of 4-carboxamido-1-methyl-$N^5$-[3-[3-(piperidinomethyl)phenoxy]propyl]-pyrazole-3,5-diamine are boiled under reflux in 150 ml of 20% aqueous hydrochloric acid for 24 hours. The reaction mixture is concentrated by evaporation under vacuum and dissolved in water. Potassium carbonate is added and the product is extracted with ethyl acetate. After dehydration over sodium sulphate and removal of the solvent by evaporation under vacuum, a brown solid remains behind, and this solid is re-crystallized from ethyl acetate.

Colourless crystals, melting point 128.5°–129.5° C.

Yield: 1.8 g (53% of theoretical)

Rf: 0.60 (silica gel; methylene chloride/methanol/TEA 85/10/5)

$C_{19}H_{28}N_4O_2$ (344) Calculated: C, 66.25; H, 8.19. Found: C, 65.91; H, 8.05.

$^1$H-NMR data: (d$_6$-DMSO, TMS as Internal standard) $\delta = 1.44$ (m) 6 H, 1.95 (m) 2 H, 2.32 (m) 4 H, 3.08 (m) 2 H, 3.19 (s) 3 H, 3.40 (s) 2 H, 4.05 (t) 2 H, 4.51 (s) 1 H, (replaceable by D$_2$O), 5.84 (t) 1 H, (replaceable by D$_2$O), 6.7–7.4 (m) 4 H, 8.4–10.0 (broad) 1 H (replaceable by D$_2$O).

EXAMPLE 2

(a) 2-cyano-3-methylthio-3-[3-[3-(pyrrolidinomethyl)phenoxy]propylamino]propene nitrile

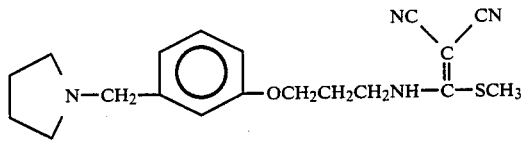

Preparation is carried out by a method analogous to that of Example 1 a.

Rf: 0.35 (Al$_2$O$_3$ neutral; ethyl acetate/petroleum ether 5/2)

$C_{19}H_{24}N_4OS$ (356)

$^1$H-NMR data: (CDCl$_3$, TMS as internal standard) $\delta = 1.80$ (m) 4 H, 2.19 (m) 2 H, 2.58 (m) 4 H, 2.62 (s) 3 H, 3.64 (s) 2 H, 3.84 (m) 2 H, 4.15 (t) 2 H, 6.6–7.4 (m) 5 H (1 H replaceable by D$_2$O) ppm.

(b)
4-cyano-1-methyl-N⁵-[3-[3-(pyrrolidinomethyl)phenoxy]propyl]-pyrazole-3,5-diamine

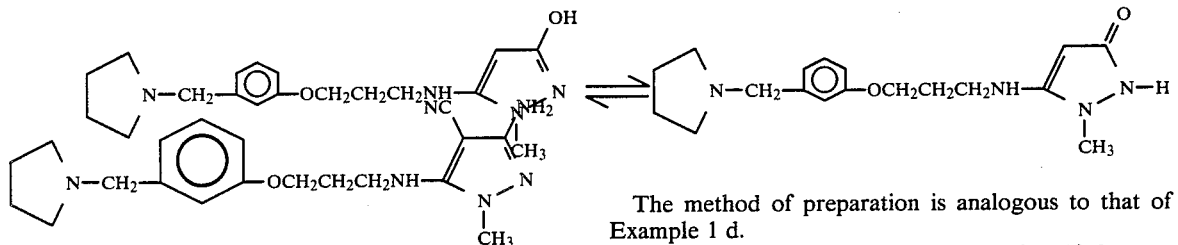

The method of preparation is analogous to that of Example 1 b.

Colourless crystals, melting point 102°–104° C.

Rf: 0.4 (Al$_2$O$_3$ neutral; ethylacetate/isopropanol 95/5)

C$_{19}$H$_{26}$N$_6$O (354)

¹H-NMR data (CDCl$_3$, TMS as internal standard) δ=1.78 (m) 4 H, 2.15 (m) 2 H, 2.52 (m) 4 H, 3.38 (s) 3 H, 3.60 (s) 2 H, 3.72 (t) 2 H, 3.97 (s) 2 H (replaceable by D$_2$O), 4.65 (t) 1 H (replaceable by D$_2$O), 6.8–7.4 (m) 4 H ppm.

(c)
4-carboxamido-1-methyl-N⁵-[3-[3-(pyrrolidinomethyl)-phenoxy]propyl]-pyrazole-3,5-diamine

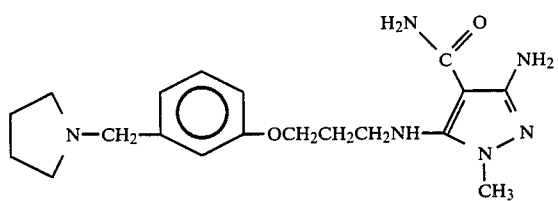

The method of preparation is analogous to that of Example 1c.

Colourless crystals, melting point 78°–80° C.

Rf: 0.24 (silica gel; ethyl acetate/methanol/TEA 85/10/5)

C$_{19}$H$_{28}$N$_6$O$_2$ (372)

¹H-NMR data: (CDCl$_3$, TMS as internal standard) δ=1.75 (m) 4 H, 2.01 (m) 2 H, 2.50 (m) 4 H, 3.35 (m) 2 H, 3.61 (s) 5 H, 3.90 (s) 2 H, (replaceable by D$_2$O), 4.07 (t) 2 H, 5.71 (t) 1 H (replaceable by D$_2$O), 6.10 (s) 2 H (replaceable by D$_2$O), 6.7–7.4 (m) 4 H ppm.

(d)
1-methyl-5-[3-[3-(pyrrolidinomethyl)phenoxy]-propylamino]-3-hydroxy 1H-pyrazole and 5-amino-1-methyl-N⁵-[3-[3-(pyrrolidinomethyl)phenoxy]propyl]-1,2-dihydro-pyrazol-3-one

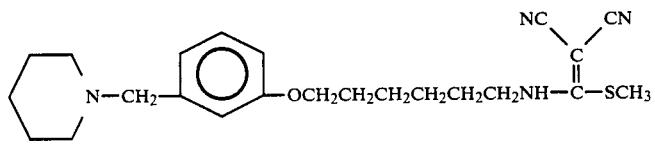

The method of preparation is analogous to that of Example 1 d.

Colourless crystals, melting point 120°–123° C.

Rf: 0.23 (silica gel; methylene chloride/methanol/TEA 100/10/5)

C$_{18}$H$_{26}$N$_4$O$_2$ (330)

¹H-NMR data: (d$_6$-DMSO, TMS as internal standard) δ=1.68 (m) 4 H, 1.96 (m) 2 H, 2.43 (m) 4 H, 3.07 (m) 2 H, 3.15 L (s) 3 H, 3.56 (s) 2 H, 4.04 (t) 2 H, 4.50 (s) 1 H (replaceable by D$_2$O), 5.86 (t) 1 H (replaceable by D$_2$O), 6.8–7.4 (m) 4 H, 6.5–9.0 (broad) 1 H (replaceable by D$_2$O) ppm

EXAMPLE 3

(a)
2-cyano-3-methylthio-3-[6-[3-(piperidinomethyl)-phenoxy]hexylamino]propene nitrile

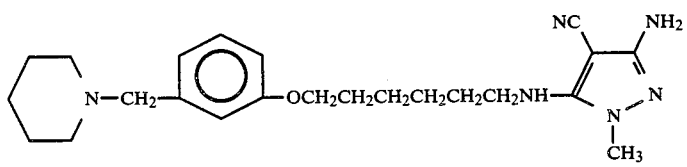

The method of preparation is analogous to that of Example 1 a.

Rf: 0.5 (Al$_2$O$_3$ neutral; ethyl acetate/petroleum ether 5/2)

C$_{23}$H$_{32}$N$_4$OS (412)

¹H-NMR data: (CDCl$_3$, TMS as internal standard) δ=1.2–2.0 (m) 14 H, 2.36 (m) 4 H, 2,64 (s) 3 H, 3.42 (s) 2 H, 3.54 (t) 2 H, 3.95 (t) 2 H, 5.5–6.3 (broad) 1 H (replaceable by D$_2$O), 6.6–7.4 (m) 4 H ppm.

(b)
4-cyano-1-methyl-N⁵-[6-[3-(piperidinomethyl)phenoxy]hexyl]-pyrazole-3,5-diamine The method of preparation is analogous to that of Example 1 b.

Colourless crystals, melting point 47°–47.5° C.

Rf: 0.55 (Al$_2$O$_3$ neutral; ethylacetate/isopropanol 95/5)

$C_{23}H_{34}N_6O$ (410)

¹H-NMR data: (CDCl₃, TMS as internal standard) δ=1.25-21. (m) 14 H, 2.37 (m) 4 H, 3.38 (s) 3 H, 3.44 (s) 2 H, 3.50 (m) 2 H, 3.7-4.2 (m) 5 H (3 H replaceable by D₂O), 6.7-7.4 (m) 4 H ppm.

(c)
4-carboxamido-1-methyl-N⁵-[6-[3-(piperidinomethyl)-phenoxy]hexyl]-pyrazole-3,5-diamine

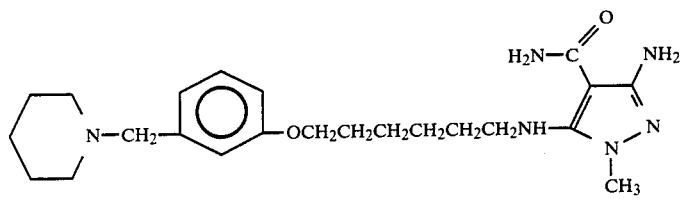

The method preparation is analogous to that of Example 1 c.

Colourless crystals, melting point 54°-56° C.

Rf: 0.36 (silica gel; ethylacetate/methanol/TEA 85/10/5).

$C_{23}H_{36}N_6O_2$ (428)

¹H-NMR data (CDCl₃, TMS as internal standard δ=1.2-2.1 (m) 14 H, 2.43 (m) 4 H, 3.23 (m) 2 H, 3.50 (s) 2 H, 3.65 (s) 3 H, 4.01 (t) 2 H, 4.10 (s) 2 H (replaceable by D₂O), 5.83 (t) 1 H (replaceable by D₂O), 6.35 (s) 2 H (replaceable by D₂O), 6.8-7.5 (m) 4 H ppm.

(d)
1-methyl-5-[6-[3-(piperidinomethyl)phenoxy]hexylamino]-3-hydroxy 1H-pyrazole and
5-amino-1-methyl-N⁵-[6-[3-(piperidinomethyl)phenoxy]hexyl]-1,2-dihydro-pyrazol-3-one

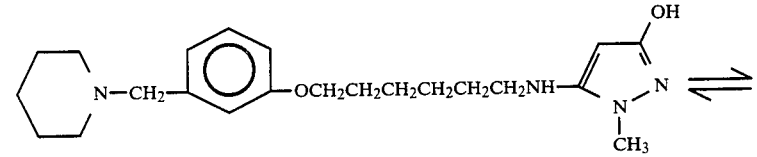

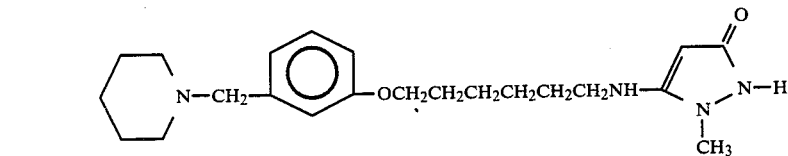

The method of preparation is analogous to that of Example 1 d.

Colourless crystals, melting point 106°-109° C.

Rf: 0.21 (silica gel; ethylacetate/methanol/TEA 85/10/5)

$C_{22}H_{34}N_4O_2$ (386)

¹H-NMR data (d₆-DMSO, TMS as internal standard) δ=1.2-2.0 (m) 14 H 2.30 (m) 4 H, 2,92 (m) 2 H, 3.09 (s) 3 H, 3.0-4.0 (broad) 1 H (replaceable by D₂O), 3.37 (s) 2 H, 3.94 (t) 2 H, 4.42 (s) 1 H (replaceable by D₂O), 5.78 (t) 1 H (replaceable by D₂O), 6.7-7.4 (m) 4 H ppm.

EXAMPLE 4

1-methyl-5-[4-[3-(piperidinomethyl)phenoxy]butylamino]-3-hydroxy-1H-pyrazole and
5-amino-1-methyl-N⁵-[4-[3-(piperidinomethyl)phenoxy]butyl]-1,2-dihydropyrazol-3-one

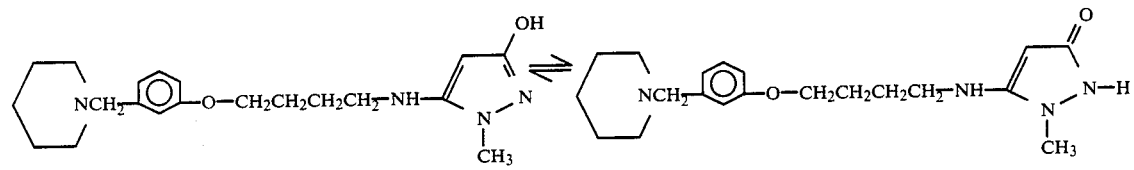

The method of preparation is analogous to that of Examples 1 a-d.

Colourless crystals, melting point 140° C.

Rf: 0.35 (silica gel; chloroform/methanol/ammonia 85/13/2)

$C_{20}H_{30}N_4O_2$ (358)

¹H-NMR data: (d₆-DMSO, TMS as internal standard) δ=1.41 (m) 6 H, 1.73 (m) 4 H, 2.30 (m) 4 H, 3.00 (m) 2 H, 3.12 (s) 3 H, 3.37 (s) 2 H, 3.97 (m) 2 H, 4.46 (s) 1 H (replaceable by D₂O), 5.81 (t) 1 H (replaceable by D₂O), 6.7-7.4 (m) 4 H, 8.7-9.5 (broad) 1 H (replaceable by D₂O) ppm.

EXAMPLE 5

1-methyl-5-[4-[3-(pyrrolidinomethyl)phenoxy]-butylamino]-3-hydroxy-1H-pyrazole and 5-amino-1-methyl-$N^5$-[4-[3-(pyrrolidinomethyl)phenoxy]butyl]-1,2-dihydro pyrazol-3-one

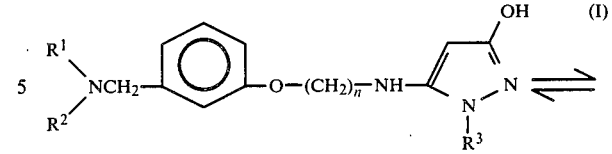
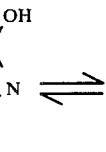
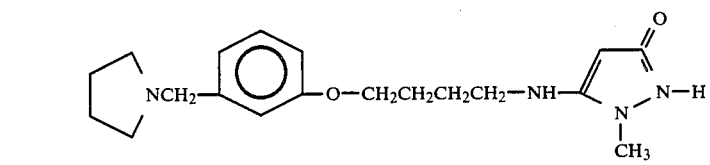
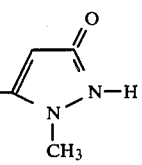

The method of preparation is analogous to that of Examples 1 a–d.

Colourless crystals, melting point 115°–116° C.
Rf: 0.33 (silica gel; chloroform/methanol/ammonia 85/13/2)
$C_{19}H_{28}N_4O_2$ (344)
$^1$H-NMR data: (d$_6$-DMSO, TMS as internal standard) δ = 1.65 (m) 8 H, 2.41 (m) 4 H, 3.0 (m) 2 H, 3.11 (s) 3 H, 3.52 (s) 2 H, 3.97 (m) 2 H, 4.46 (s) 1 H (replaceable by D$_2$O) 5.82 (m) 1 H (replaceable by D$_2$O) 6.7–7.4 (m) 4 H, 8.5–9.7 (broad) 1 H (replaceable by D$_2$O) ppm.

EXAMPLE 6

1-ethyl-5-[3-[3-(piperidinomethyl)phenoxy]-propylamino]-3-hydroxy-1H-pyrazole and 5-amino-1-ethyl-$N^5$-[3-[3-(piperidinomethyl)phenoxy]-propyl]-1,2-dihydro-pyrazol-3-one

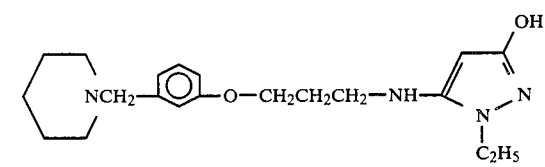
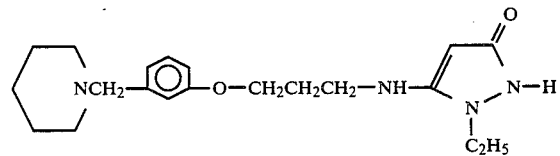

The method of preparation is analogous to that of Examples 1 a–d, using ethyl hydrazine.

Colourless crystals melting point 134°–135° C.
Rf: 0.50 (silica gel; chloroform/methanol/ammonia 85/13/2)
$C_{20}H_{30}N_4O_2$ (358)
$^1$H-NMR data: (d$_6$-DMSO, TMS as internal standard) δ = 1.06 (t) 3 H, 1.43 (m) 6 H, 1.96 (m) 2 H, 2.32 (m) 4 H, 3.12 (m) 2 H, 3.40 (s) 2 H, 3.50 (q) 2 H, 4.03 (t) 2 H, 4.49 (s) 1 H, (replaceable by D$_2$O), 5.93 (t) 1 H (replaceable by D$_2$O), 6.7–7.4 (m) 4 H, 8.5–9.5 (broad) 1 H (replaceable by D$_2$O) ppm.

We claim:
1. A compound of the formula I

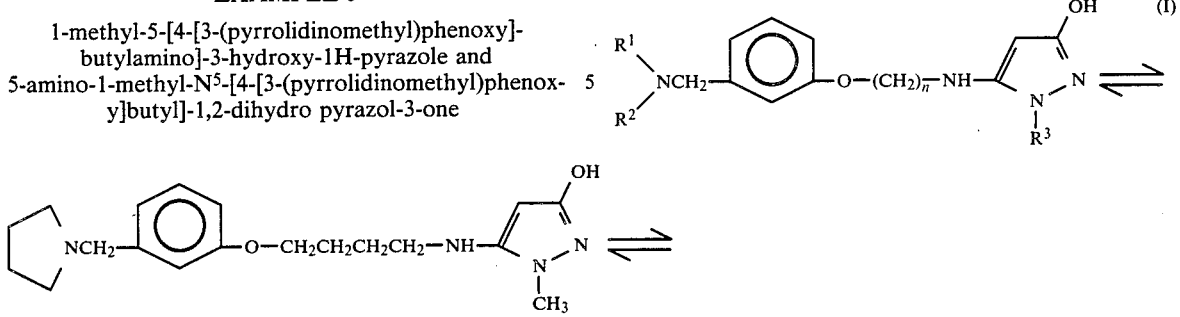

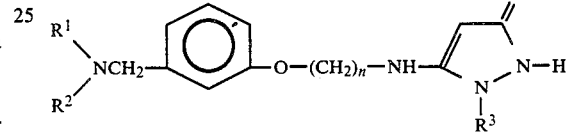

wherein $R^1$ and $R^2$ denote, independently of one another, a hydrogen atom or a straight chain or branched $C_1$–$C_3$ alkyl group or $R^1$ and $R^2$ together with the nitrogen atom denotes a 4- to 7-membered heterocyclic ring containing one nitrogen heteroatom, n represents an integer having a value from 2 to 6, and $R^3$ denotes a hydrogen atom or a methyl or ethyl group, and the physiologically acceptable salts and hydrates thereof.

2. A compound according to claim 1, characterised in that $R^1$ and $R^2$ together with the nitrogen atom denote a 5- to 6-membered heterocyclic ring, n represents the number 3 and $R^3$ represents methyl, and the physiologically acceptable salts and hydrates thereof.

3. 1-methyl-5-[3-[3-(piperidinomethyl)phenoxy]-propylamino]-3-hydroxy-1H-pyrazole and the physiologically acceptable salts thereof.

4. A process for the preparation of a pyrazole compound comprising the reaction of a compound corresponding to the formula:

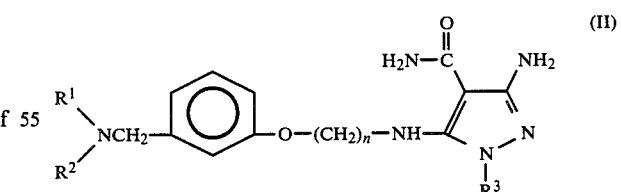

in aqueous acid solution to form a compound having the formula:

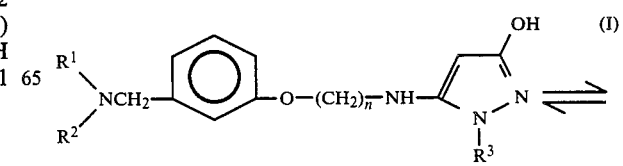

-continued

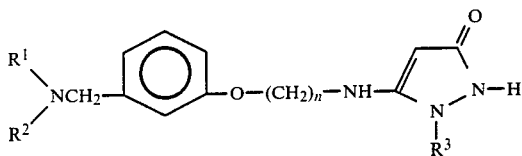

and optionally converting the compound obtained into a physiologically acceptable salt thereof wherein $R^1$ and $R^2$ denote, independently of one another, a hydrogen atom or a straight chain or branched $C_1$-$C_3$ alkyl group or $R^1$ and $R^2$ together with the nitrogen atom denote a 4- to 7-membered heterocyclic ring containing one nitrogen heteroatom, n represents an integer having a value from 2 to 6, and $R^3$ denotes a hydrogen atom or a methyl or ethyl group.

5. Pharmaceutical preparation for the treatment of gastric disturbances characterised in that it contains a compound according to one of the claims 1 to 3 together with at least one inert pharmaceutically acceptable carrier or diluent, said preparation containing a histamine $H_2$ receptor inhibiting amount of the compound.

* * * * *